US010799656B2

(12) United States Patent
Berry Ann et al.

(10) Patent No.: US 10,799,656 B2
(45) Date of Patent: Oct. 13, 2020

(54) PATIENT INTERFACE ASSEMBLY DISCONNECT DETECTION

(71) Applicant: KONINKLIJKE PHILIPS N.V., Eindhoven (NL)

(72) Inventors: Nathan John Berry Ann, Cranberry Township, PA (US); William Anthony Truschel, Oakmont, PA (US)

(73) Assignee: Koninklijke Philips N.V., Eindhoven (NL)

(*) Notice: Subject to any disclaimer, the term of this patent is extended or adjusted under 35 U.S.C. 154(b) by 1413 days.

(21) Appl. No.: 14/422,012

(22) PCT Filed: Aug. 13, 2013

(86) PCT No.: PCT/IB2013/056608
§ 371 (c)(1),
(2) Date: Feb. 17, 2015

(87) PCT Pub. No.: WO2014/030098
PCT Pub. Date: Feb. 27, 2014

(65) Prior Publication Data
US 2015/0182710 A1  Jul. 2, 2015

Related U.S. Application Data

(60) Provisional application No. 61/684,991, filed on Aug. 20, 2012.

(51) Int. Cl.
*A61M 16/00* (2006.01)
*A61M 16/06* (2006.01)

(52) U.S. Cl.
CPC .... *A61M 16/0003* (2014.02); *A61M 16/0051* (2013.01); *A61M 16/0066* (2013.01);
(Continued)

(58) Field of Classification Search
CPC .......... A61M 16/0003; A61M 16/0066; A61M 16/06; A61M 16/0051; A61M 16/0063;
(Continued)

(56) References Cited

U.S. PATENT DOCUMENTS 5,881,717 A   3/1999  Isaza
5,931,160 A   8/1999  Gilmore
(Continued)

FOREIGN PATENT DOCUMENTS

JP   2008543384 A    12/2008
WO  WO2006133494 A1  12/2006
(Continued)

OTHER PUBLICATIONS

Hartley H.O., "The Modified Gauss-Newton Method for the Fitting of Non-Linear Regression Functions by Least Squares", Technometrics, vol. 3, No. 2, (May 1961), pp. 269-280 http://dx.doi.org/10.1080/00401706.1961.10489945.
(Continued)

*Primary Examiner* — Samchuan C Yao
*Assistant Examiner* — Margaret M Luarca
(74) *Attorney, Agent, or Firm* — Daniel H. Brean (57) ABSTRACT

A flow of breathable gas is delivered to a subject through a patient interface assembly. An enhanced technique for determining whether the airway of subject is disengaged from the patient interface assembly. A model that provides predicted values of a dynamic property of the flow of breathable gas is fit to measured values of the dynamic property. The model and/or the fit of the predicted values to the measured values are then analyzed to determine whether or not the airway of the subject is disengaged from the patient interface assembly. This provide enhanced determination of these conditions even in implementations in which a restrictive patient interface assembly is used.

21 Claims, 5 Drawing Sheets

(52) U.S. Cl.
CPC ......... *A61M 16/026* (2017.08); *A61M 16/06*
(2013.01); *A61M 16/0063* (2014.02); *A61M*
*2016/003* (2013.01); *A61M 2016/0027*
(2013.01); *A61M 2205/13* (2013.01); *A61M*
*2205/3334* (2013.01); *A61M 2205/502*
(2013.01)

(58) Field of Classification Search
CPC ...... A61M 2205/3334; A61M 2205/14; A61M 2205/15
See application file for complete search history.

(56) References Cited

U.S. PATENT DOCUMENTS

| | | | |
|---|---|---|---|
| 6,668,824 B1 | 12/2003 | Isaza | |
| 7,984,712 B2 | 7/2011 | Soliman | |
| 2006/0000475 A1* | 1/2006 | Matthews | ......... A61M 16/0051 128/204.21 |
| 2010/0147303 A1 | 6/2010 | Jafari | |

FOREIGN PATENT DOCUMENTS

| | | |
|---|---|---|
| WO | WO2009123974 A1 | 10/2009 |
| WO | WO2011100215 A1 | 8/2011 |

OTHER PUBLICATIONS

Brunner J.X. et al., "Prototype Ventilator and Alarm Algorithm for the NASA Space Station", Journal of Clinical Monitoring and Computing, vol. 5, No. 2, pp. 90-99, Apr. 1989 http://www.springerlink.com/content/r0527051240u5118/.

* cited by examiner

PATIENT INTERFACE ASSEMBLY DISCONNECT DETECTION

CROSS-REFERENCE TO RELATED APPLICATIONS

This patent application claims the priority benefit under 35 U.S.C. 0 371 of international patent application no. PCT/IB2013/056608, Aug. 13, 2013, claims the priority benefit under 35 U.S.C. § 119(e) of U.S. Provisional Application No. 61/684,991 filed on Aug. 20, 2012, the contents of which are herein incorporated by reference.

BACKGROUND OF THE INVENTION

1. Field of the Invention

The present disclosure pertains to determining whether a patient circuit is disengaged from a ventilator in implementations in which a restrictive patient interface assembly is used to engage the subject's airway.

2. Description of the Related Art

When ventilating a subject with a ventilator, the pressure of a flow of breathable gas provided to the subject via a patient interface asembly is typically controlled in accordance with a therapy regime. In order to ensure that the airway of the subject is engaged with the patient interface assembly to which the patient circuit is connected and through which the flow of breathable gas is being delivered, a flow rate is typically monitored. If the flow rate rises above some threshold level, then it is determined that the airway of the subject is not engaged with the patient interface assembly.

In implementations in which a restrictive patient interface is employed, however, the increase in flow rate caused by disengagement of the airway from the patient interface may be marginal. In such implementations (and/or in other implementations), the conventional technique for detecting whether the airway is engaged with the patient interface may not provide a requisite precision and/or accuracy.

SUMMARY OF THE INVENTION

Accordingly, one or more aspects of the present disclosure relate to a ventilator. In some embodiments, the ventilator comprises one or more of a pressure generator, a subject interface, one or more sensors, and one or more processors. The pressure generator is configured to generate a pressurized flow of breathable gas for delivery to the airway of a subject. The subject interface is configured to convey the pressurized flow of breathable gas from the pressure generator to the airway of the subject. The one or more sensors are configured to generate output signals conveying information related to a first dynamic property of the pressurized flow of breathable gas. The one or more processors are configured to execute computer program modules. The computer program modules comprise a control module, a property determination module, a model parameter module, and a disconnect detection module the control module is configured to control the pressure generator to adjust a second dynamic property of the pressurized flow of breathable gas over time in accordance with a therapy regime. The property determination module is configured to determine measured values of the first dynamic property of the pressurized flow of breathable gas during respiration of the subject such that measured values of the first dynamic property are determined for individual points of time in an ongoing manner. The model parameter module is configured to determine, for individual periods of time, parameter values for a model parameter of a model that provides a predicted value of the first dynamic property at a point in time as a function of the second dynamic property at the same point in time. The model parameter module is configured to determine a parameter value for the model parameter during a given period of time by correlating predicted values of the first dynamic property to measured values of the first dynamic property for points of time that occurred in the given period of time. A disconnect detection module is configured to determine whether the airway of the subject is engaged with the subject interface to receive the pressurized flow of breathable gas based on correlation of predicted values of the first dynamic property with measured values of the first dynamic property.

Yet another aspect of the present disclosure relates to determining whether a subject is receiving a pressurized flow of breathable gas from a ventilator. The method is implemented by a ventilator comprising a pressure generator, a subject interface, one or more sensors, and one or more processors. The method comprises generating, with the pressure generator, a pressurized flow of breathable gas for delivery to the airway of a subject; conveying the pressurized flow of breathable gas from the pressure generator to the airway of the subject through the subject interface; generating, with the one or more sensors, output signals conveying information related to a first dynamic property of the pressurized flow of breathable gas; controlling, with the one or more processors, the pressure generator to adjust a second dynamic property of the pressurized flow of breathable gas over time in accordance with a therapy regime; determining, with the one or more processors, measured values of the first dynamic property of the pressurized flow of breathable gas during respiration of the subject such that measured values of the first dynamic property are determined for individual points of time in an ongoing manner; determining, with the one or more processors for individual periods of time, parameter values for a model parameter of a model that provides a predicted value of the first dynamic property at a point in time as a function of the second dynamic property at the same point in time, wherein determination of a parameter value for the model parameter during a given period of time includes correlating predicted values of the first dynamic property to measured values of the first dynamic property for points of time that occurred in the given period of time; and determining, with the one or more processors, whether the airway of the subject is engaged with the subject interface to receive the pressurized flow of breathable gas based on correlation of predicted values of the first dynamic property with measured values of the first dynamic property.

Still another aspect of present disclosure relates to a system for determining whether a subject is receiving a pressurized flow of breathable gas from a ventilator. In some embodiments, the system comprises means for generating a pressurized flow of breathable gas for delivery to the airway of a subject; means for conveying the pressurized flow of breathable gas from the pressure generator to the airway of the subject; means for generating output signals conveying information related to a first dynamic property of the pressurized flow of breathable gas; means for controlling the pressure generator to adjust a second dynamic property of the pressurized flow of breathable gas over time in accordance with a therapy regime; means for determining measured values of the first dynamic property of the pressurized flow of breathable gas during respiration of the subject such that measured values of the first dynamic property are determined for individual points of time in an ongoing manner; means for determining, for individual periods of time, parameter values for a model parameter of a model that provides a predicted value of the first dynamic property at a point in time as a function of the second dynamic property at the same point in time, wherein the means for determining parameter values is configured to determine a parameter value for the model parameter during a given period of time by correlating predicted values of the first dynamic property to measured values of the first dynamic property for points of time that occurred in the given period of time; and means for determining whether the airway of the subject is engaged with the subject interface to receive the pressurized flow of breathable gas based on correlation of predicted values of the first dynamic property with measured values of the first dynamic property.

These and other objects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the disclosure.

DETAILED DESCRIPTION OF EXEMPLARY EMBODIMENTS

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

Figure 1:
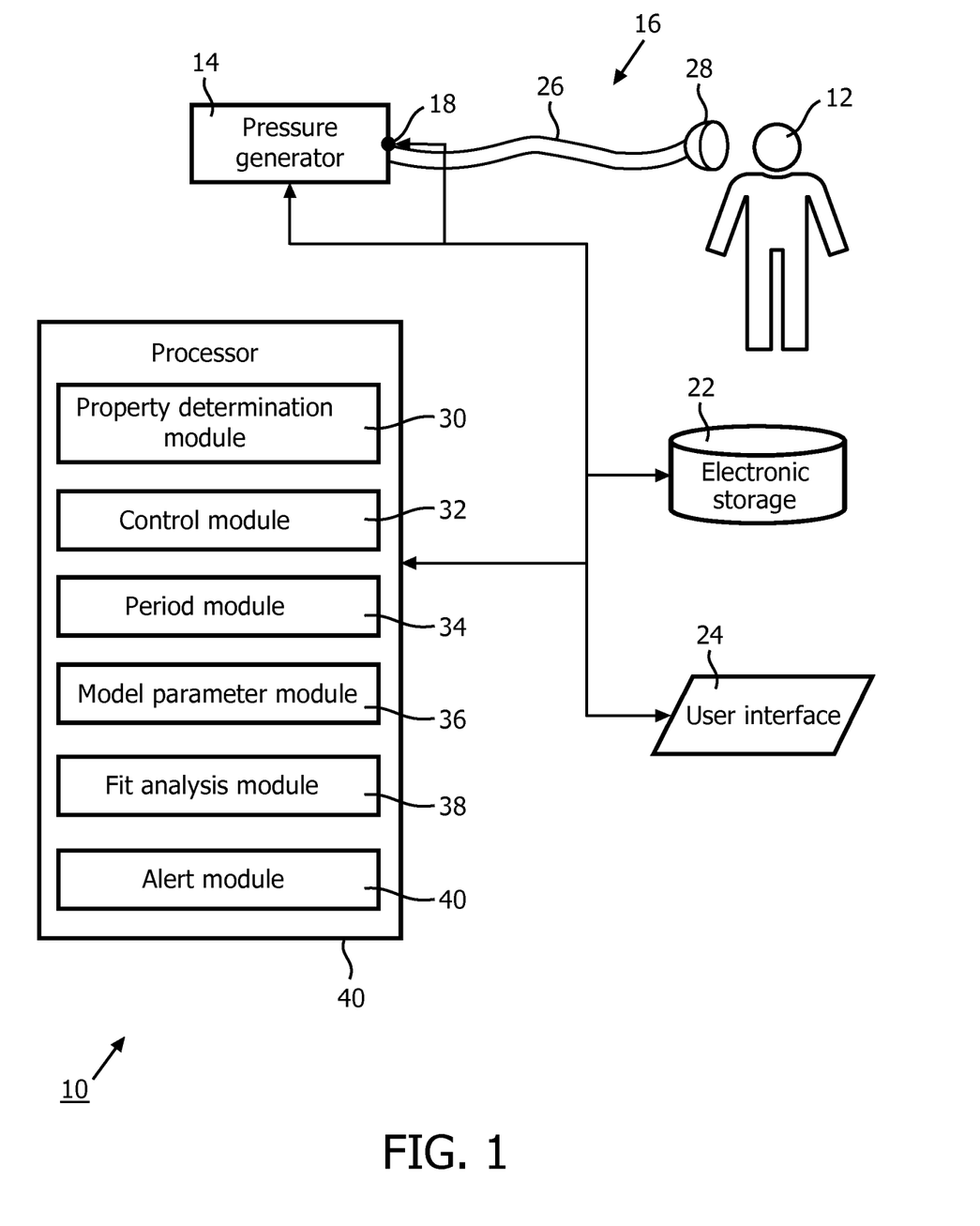
FIG. 1 illustrates a system configured to provide a flow of breathable gas to a subject.

FIG. 1 illustrates a system 10 configured to provide a flow of breathable gas to a subject 12. The flow of breathable gas may ventilate 12. That is the flow of breathable gas may provide at least partial mechanical ventilation of subject 12 such that the breathing of subject is supported and/or facilitated by the flow of breathable gas. System 10 implements an enhanced technique for determining whether the airway of subject 12 is receiving the flow of breathable gas, or if the airway of subject 12 has been disengaged from system 10. System 10 may provide enhanced determination of these conditions even in implementations in which a restrictive interface is used to interface system 10 with the airway of subject 12. In some implementations, system 10 may include one or more of a pressure generator 14, a patient interface 16, one or more sensors 18, one or more processors 20, electronic storage 22, a user interface 24, and/or other components.

Pressure generator 14 is configured to generate a flow of breathable gas for delivery to the airway of subject 12. Pressure generator 14 may control one or more dynamic parameters of the flow of breathable gas (e.g., flow rate, pressure, volume, humidity, temperature, gas composition, etc.) for therapeutic purposes, or for other purposes. The one or more parameters may be controlled in accordance with a therapy regime (e.g., as discussed further below). The therapy regime may be configured to sustain and/or otherwise improve the quality of life in subject 12.

By way of non-limiting example, pressure generator 14 may be configured to control the pressure of the flow of breathable gas in order to provide mechanical respiration to subject 12 according to a ventilation therapy regime. Pressure generator 14 may include one or more of a bellows, a blower, a compressor, a pressurized gas source (e.g., wall gas, a Dewar, and/or other gas sources), and/or other mechanisms for pressurizing gas.

The flow of breathable gas is delivered to the airway of subject 12 via patient interface assembly 16. Patient interface assembly 16 is configured to communicate the flow of breathable gas generated by pressure generator 14 to the airway of subject 12. As such, patient interface assembly 16 includes a patient circuit 26 and an interface appliance 28. Patient circuit 26, which is typically a flexible conduit, conveys the flow of breathable gas to interface appliance 28, and interface appliance 28 delivers the flow of breathable gas to the airway of subject 12.

Some examples of interface appliance 28 may include, for example, an endotracheal tube, a nasal mask, a nasal/oral mask, a full face mask, a total face mask, or other interface appliances that communication a flow of gas with an airway of a subject. The present invention is not limited to these examples, and contemplates delivery of the flow of breathable gas to subject 12 using any interface appliance.

In the embodiments illustrated in FIG. 1, patient interface assembly 16 is a single-limbed system in which gas received from the airway of subject 12 during exhalation is exhausted through a single conduit. It will be appreciated that this is not intended to be limiting, as ventilation, and/or other forms of respiratory therapy, may be realized using other configurations such as a dual-limbed circuit.

One or more sensors 18 of system 10 in FIG. 1 are configured to generate output signals conveying measurements related to dynamic properties of the flow of breathable gas. These dynamic properties may include one or more of flow rate, pressure, humidity, velocity, acceleration, composition and/or other gas or dynamic gas properties. As depicted in FIG. 1, one or more sensors 18 may be in fluid communication with conduit 26 and/or interface appliance 28. The illustration of sensors 18 including one member in FIG. 1 is not intended to be limiting. The illustration of sensors 18 at or near pressure generator 14 is not intended to be limiting. Sensors 18 may include a plurality of members and/or sensors 18 may be disposed at a variety of locations within system 10.

In some embodiments, sensors 18 may generate output signals that convey information related to one or more dynamic properties of the flow of breathable gas indirectly. For example, the output signals may vary as a function of a dynamic property of a component of pressure generator 14 (or of a device that pressure generator 14 is integrated, combined, or coupled with) such as valve drive current, rotor speed, motor speed, blower speed, fan speed, or a related measurement that may serve as a proxy for any dynamic gas property through a previously known and/or (calibrated) mathematical relationship. Resulting signals or information from the one or more sensors 18 may be transmitted to 20, user interface 24, electronic storage 22, and/or other components of system 10. This transmission may be wired and/or wireless.

Processor 20 is configured to execute one or more computer program modules. The one or more computer program modules may include one or more of a property determination module 30, a control module 32, a period module 34, a model parameter module 36, a disconnect detection module 38, an alert module 40, and/or other modules.

Property determination module 30 is configured to determine measured values of the dynamic properties of the flow of breathable gas. The measured values are determined based on the output signals generated by sensors 18. The measured values are determined for individual points of time in an ongoing manner. The individual points of time may occur periodically (e.g., at a sampling rate), intermittently, and/or at other intervals. The dynamic properties may include one or more of flow rate, pressure, volume, humidity, temperature, gas composition, and/or other properties.

Control module 32 is configured to control pressure generator 14 to adjust one or more dynamic properties of the flow of breathable gas in accordance with the pressure regime. In some embodiments, control module 32 is configured to control either pressure or flow rate to facilitate ventilation of subject 12. Control module 32 implements the measured values of the dynamic property (or properties) being controlled in a feedback manner to ensure that a current value of the dynamic property (or properties) being controlled correspond to values dictated by the therapy regime.

Period module 34 is configured to define periods of time. In the individual periods of time defined by period module 34, a series of points in time at which measured values are determined by property determination module 30 may occur. The periods of time may coincide with events in the respiration of subject 12. For example, a period of time may coincide with an integer number of breaths of subject 12 (e.g., 1 breath, 2 breaths, etc.), an inhalation, an exhalation, and/or other breathing events. In such implementations, period module 34 may determine the beginning and/or end of the time periods based on control of pressure generator 14 by control module 32, based on determinations of measured values of one or more dynamic properties by property determination module 30, and/or by other techniques. In some implementations, the time periods may be defined at a specific frequency, may be defined with a specific period, may include a specific number of points in time at which measured values are determined, and/or may have other defined characteristics.

Model parameter module 36 is configured to fit a model that provides predicted values of a first dynamic property of the flow of breathable gas to measured values of the first dynamic property of the flow of breathable gas. The model may provide predicted values of the first dynamic property based on measured values of a second dynamic property of the flow of breathable gas. For example, the first and second dynamic properties of the flow of breathable gas may include flow rate and/or pressure. The model may be a model of pressure generator 14 and/or patient interface assembly 16 when the airway of subject 12 is not engaged with patient interface assembly 16 (e.g., when subject 12 has been disconnected from system 10).

Model parameter module 36 performs this fit by determining parameter values for one or more model parameters of the model that provide a best fit of the predicted values to the measured values during individual periods of time. As such, separate parameter values (or sets of parameter values) may be determined for the model parameter(s) for the separate periods of time.

By way of non-limiting example, a first order model of the circuit formed by pressure generator 14 and/or patient interface assembly 16 without the airway of subject 12 being engaged therewith may be expressed as:

$$Q_{pr} = C(P_o)^Y; \quad (1)$$

where $Q_{pr}$ represents a predicted flow rate for a point in time, C represents orifice conductance at interface appliance 28, $P_o$ represents pressure across interface appliance 28 for the point in time, and y represents a pressure exponent term. If the pressure drop along conduit 26 and interface appliance 28 is neglected, then $P_o$ can be approximated as the measured value of pressure (e.g., at an outlet of pressure generator 14).

Using this model, and the measured values of pressure for a period of time (e.g., a breath), a linear regression can be performed to determine the parameter values for □ and C that provide a best fit to the measured values of flow rate during the period of time. The goal of such a calculation would be to minimize the sum of squares, S, below where the points of time, i, in the period of time run from 1 to n:

$$S = \sum_{i=1}^{n} (Q_i - B1(P_i)^{B2})^2 = \sum_{i=1}^{n} (r_i)^2; \quad (2)$$

where $Q_i$ represents the measured value of flow rate at the point in time i, B1 represents the modeled orifice conductance for the period of time, $P_i$ represents the measured value for pressure at the point in time i, and B2 represents the modeled pressure exponent term for the period of time. This minimization may be performed by any number of techniques. For example, a Gauss-Newton iteration method, or another technique may be implemented. It will be appreciated that the description herein of using flow rate as the dynamic property for which predicted values are fit to a measured value is not intended to be limiting.

Other dynamic properties may be used in place of flow rate. For example, the concepts described herein could be implemented using flow rate, or other dynamic properties, without departing from the scope of this disclosure. It should also be appreciated that the first order model used for illustrative purposes above is not intended to be limiting. Another model having more or less model parameters for which parameter values must be determined (e.g., on a per period of time basis) may be implemented.

Disconnect detection module 38 is configured to determine whether the airway of subject 12 is engaged with patient interface assembly 16 to receive the flow of breathable gas based on the fit of predicted values of a dynamic property provided by the model using the determined parameter values to measured values of the dynamic property. Since the model models the flow of breathable gas through pressure generator 14 and/or patient interface assembly 16 without subject 12 being engaged therewith, relatively high correlation between the predicted values and the measured values indicates that the airway of subject 12 is not engaged (or not properly engaged) with patient interface assembly 16. Conversely, relatively low correlation between the predicted values and the measured values indicates that the airway of subject 12 is engaged with patient interface assembly 16, as the model does not account for the airway of subject 12 being included in the circuit.

Figure 2:
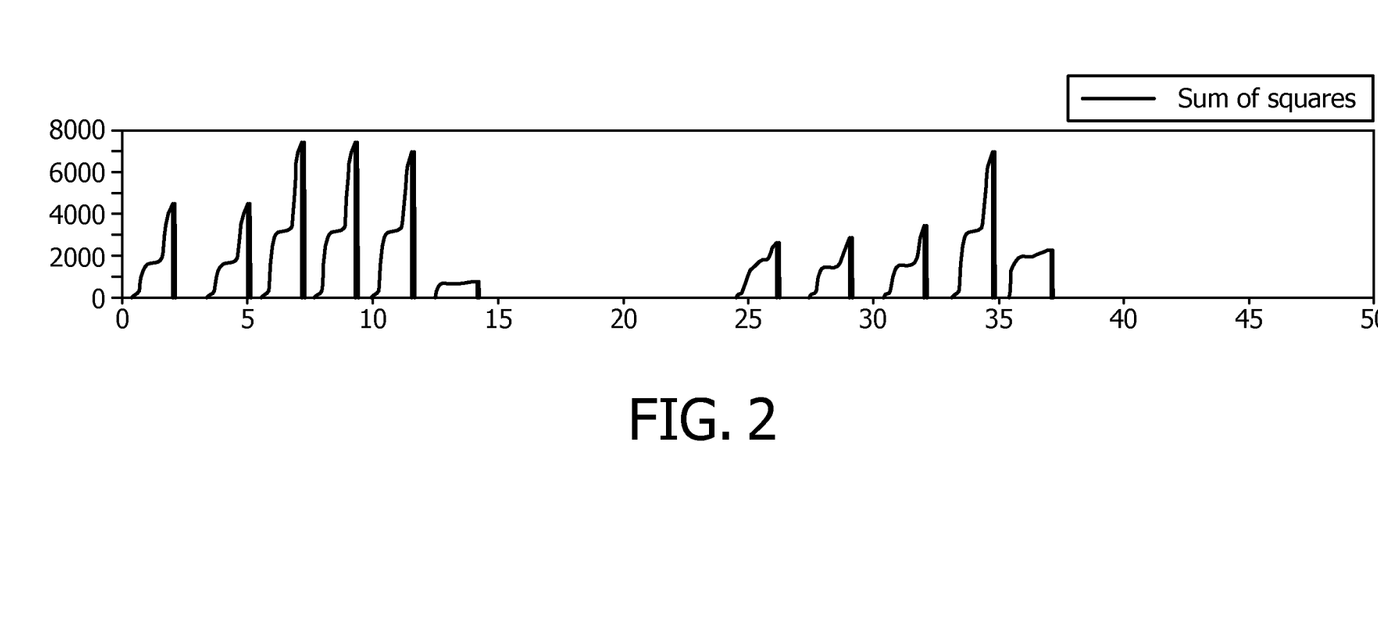
FIG. 2 is a plot of a sum of least squares between measured values and predicted values of a dynamic property of a flow of breathable gas.
Figure 3:
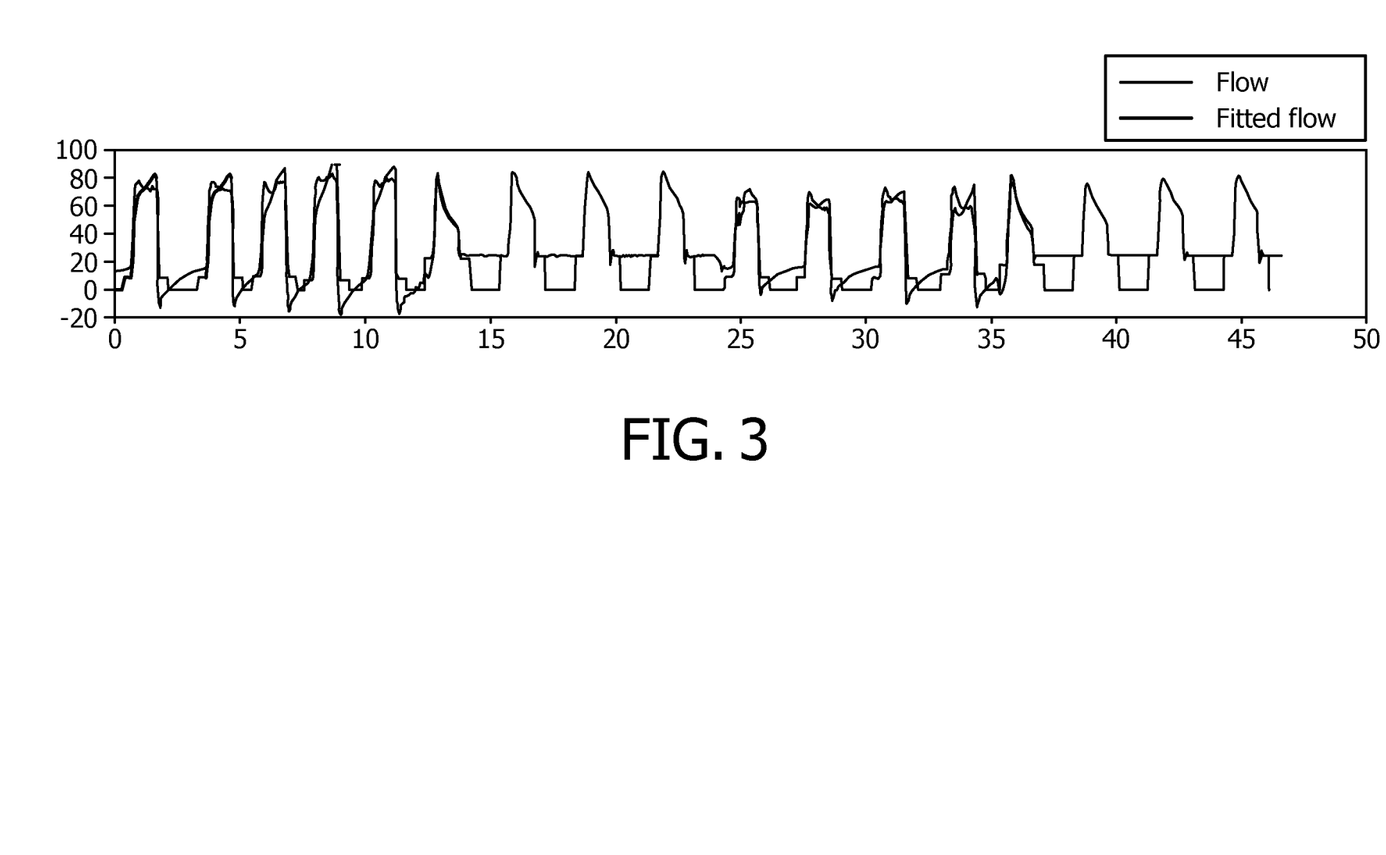
FIG. 3 is a plot of measured values and predicted values of a dynamic property of a flow of breathable gas.

By way of illustration, FIG. 2 is a plot of S over a 50 second time span. In the plot shown in FIG. 2, the periods of time for which parameter values have been determined correspond to individual breaths. During the 50 second time span plotted in FIG. 2, the patient interface assembly was disengaged from a simulated subject airway between 12 and 25 seconds, and between 37 and 47 seconds. As can be seen in FIG. 2, these stretches when the patient interface assembly was disengaged are denoted by a much better fit of the model to the measured flow rate. As further illustration, FIG. 3 is a plot of measured values of flow rate and predicted values of flow rate from the same 50 second span. It can be seen from this plot that the measured values correlate closer to the predicted values for the stretches of time during which the patient interface assembly was disengaged from the simulated airway.

In some embodiments, disconnect detection module 38 is configured obtain (e.g., determine, receive, access, etc.) a level of correlation between the predicted values and the measured values during a period of time, and then to compare the level of correlation with some threshold level. Responsive to the level of correlation indicating correlation greater than the threshold level, disconnect detection module 38 is configured to detect that patient interface assembly 16 is disengaged from the airway of subject 12. Responsive to the level of correlation indicating correlation less than the threshold level, disconnect detection module 38 is configured to detect that patient interface assembly 16 is disengaged from the airway of subject 12. The level of correlation may include, for example, the sum of squares S, some value derived therefrom (e.g., an average over a number of periods of time, etc.), and/or other levels of correlation.

It will be appreciated that the description of direct analysis of the fit between the predicted values and the measured values of the dynamic property is not the only manner in which disconnect detection module 38 may use the fit between the model and the measured values to determine whether the patient interface assembly 16 has become disengaged from the airway of subject 12. For example, since the model does not take into account the airway of subject 12, if the airway of subject 12 is coupled to the patient interface assembly 16 one or more of the model parameters may take on values that provide evidence the model is straining to account for the airway. In some implementations, rather than looking directly at the fit between the measured and predicted values, disconnect detection module 38 may look at the parameter values determined during the periods of time to detect these periods at which the parameter values indicate the model is being fitted to a circuit for which it was not intended.

Figure 4:
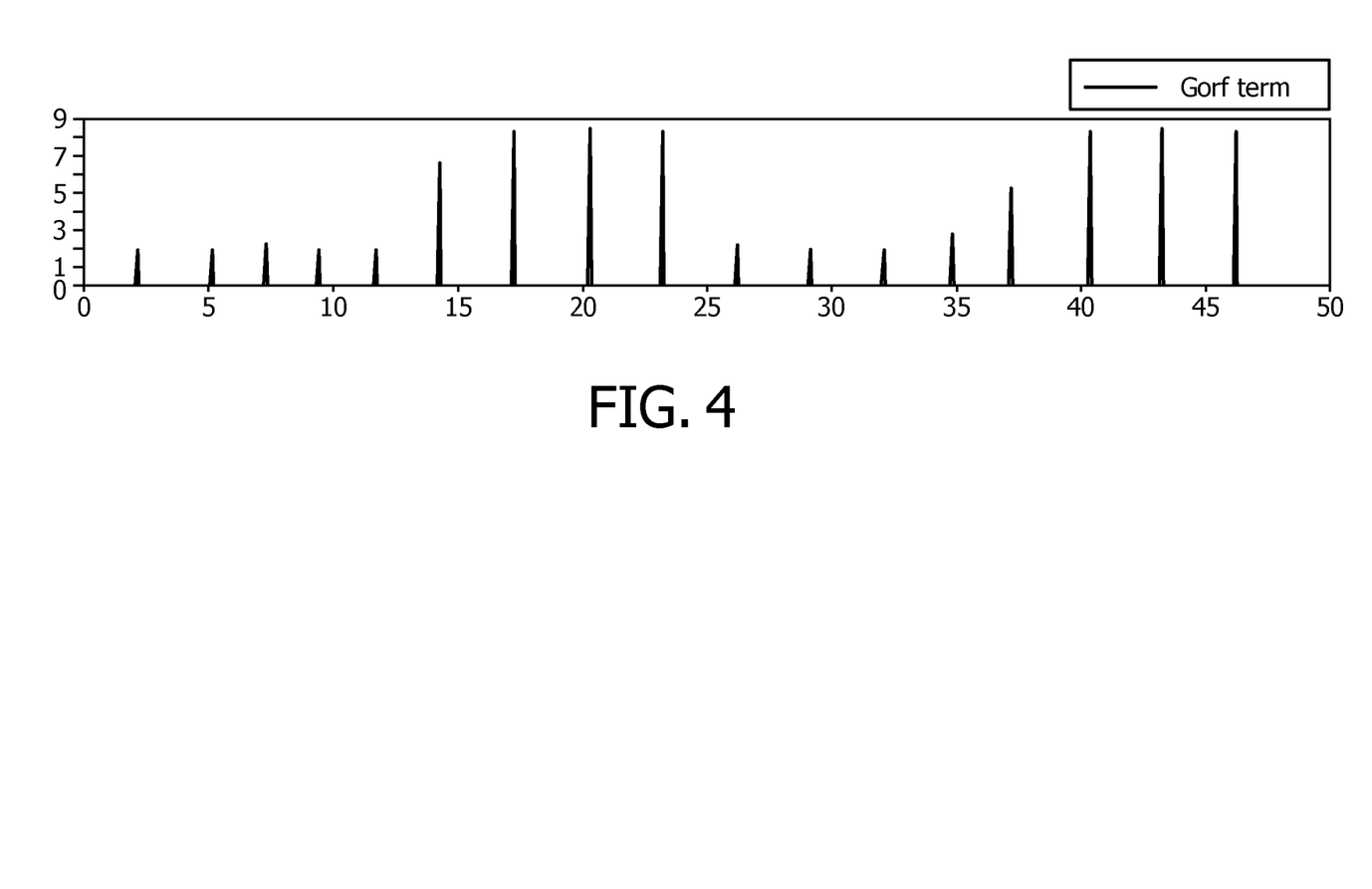
FIG. 4 is a plot of a parameter value of a model that provides predicted values of a first dynamic property of a flow of breathable gas as a function of a second dynamic property of a flow of breathable gas.

By way of illustration, FIG. 4 illustrates a plot of the C parameter value for the same 50 second span referred to with respect to FIGS. 2 and 3. As can be seen in FIG. 4, the C parameter becomes substantially larger during the stretches of time (12-25 seconds and 37-47 seconds) at which the patient interface assembly was disengaged from the simulated airway. As such, determination of the disengagement may be made by comparing the C parameter to a threshold and/or some other technique for detecting an elevated level of the C parameter.

Returning to FIG. 1, alert module 40 is configured to generate alerts indicating when the airway of subject 12 is disengaged from patient interface assembly 16. This include generating the alerts responsive to a detection by disconnect detection module 38 by the airway of subject 12 is disengaged from patient interface assembly 16. By way of non-limiting example, the alerts may be generated through user interface 24, via an electronic message (e.g., to a care provider or other user), and/or through other means. The alerts may include visual alerts, audible alerts, tactile alerts, textual alerts, and/or other alerts.

Processor(s) 20 is configured to provide information processing capabilities in system 10. As such, processor 20 may include one or more of a digital processor, an analog processor, a digital circuit designed to process information, an analog circuit designed to process information, a state machine, and/or other mechanisms for electronically processing information. Although processor 20 is shown in FIG. 1 as a single entity, this is for illustrative purposes only. In some implementations, processor 20 may include a plurality of processing units. These processing units may be physically located within the same device, or processor 20 may represent processing functionality of a plurality of devices operating in coordination. Processor 20 may be configured to execute modules 30, 32, 34, 36, 38, and/or 40. Processor 20 may be configured to execute modules 30, 32, 34, 36, 38, and/or 40 by software; hardware; firmware; some combination of software, hardware, and/or firmware; and/or other mechanisms for configuring processing capabilities on processor 20.

It should be appreciated that although modules 30, 32, 34, 36, 38, and 40 are illustrated in FIG. 1 as being co-located within a single processing unit, in implementations in which processor 20 includes multiple processing units, one or more of modules 16, 18, 20, 22, 24, 26, 28, 30, and/or 32 may be located remotely from the other modules. The description of the functionality provided by the different modules 30, 32, 34, 36, 38, and/or 40 described below is for illustrative purposes, and is not intended to be limiting, as any of modules 30, 32, 34, 36, 38, and/or 40 may provide more or less functionality than is described. For example, one or more of modules 30, 32, 34, 36, 38, and/or 40 may be eliminated, and some or all of its functionality may be provided by other ones of modules 30, 32, 34, 36, 38, and/or 40. As another example, processor 20 may be configured to execute one or more additional modules that may perform some or all of the functionality attributed below to one of modules 30, 32, 34, 36, 38, and/or 40.

Electronic storage 22 may comprise electronic storage media that electronically stores information. The electronic storage media of electronic storage 22 may include one or both of system storage that is provided integrally (i.e., substantially non-removable) with system 10 and/or removable storage that is removably connectable to system 10 via, for example, a port (e.g., a USB port, a firewire port, etc.) or a drive (e.g., a disk drive, etc.). Electronic storage 22 may include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. Electronic storage 22 may include one or more virtual storage resources (e.g., cloud storage, a virtual private network, and/or other virtual storage resources). Electronic storage 22 may store software algorithms, information determined by processor 20, information received from user interface 24, and/or other information that enables system 10 to function as described herein.

User interface 24 is configured to provide an interface between system 10 and users through which users may provide information to and receive information from system 10. Users may comprise, for example, subject 12, a caregiver, a doctor, and/or other users. This enables data, cues, results, and/or instructions and any other communicable items, collectively referred to as "information," to be communicated between a user and processor 20, electronic storage 22, and/or other components of system 10.

Examples of interface devices suitable for inclusion in user interface 24 comprise a keypad, buttons, switches, a keyboard, knobs, levers, a display screen, a touch screen, speakers, a microphone, an indicator light, an audible alarm, a printer, a tactile feedback device, and/or other interface devices. In one embodiment, user interface 24 comprises a plurality of separate interfaces. In one embodiment, user interface 24 comprises at least one interface that is provided integrally with pressure generator 14.

It is to be understood that other communication techniques, either hard-wired or wireless, are also contemplated by the present disclosure as user interface 24. For example, the present disclosure contemplates that user interface 24 may be integrated with a removable storage interface provided by electronic storage 22. In this example, information may be loaded into system 10 from removable storage (e.g., a smart card, a flash drive, a removable disk, etc.) that enables the user(s) to customize the implementation of system 10. Other exemplary input devices and techniques adapted for use with system 10 as user interface 24 comprise, but are not limited to, an RS-232 port, RF link, an IR link, modem (telephone, cable or other). In short, any technique for communicating information with system 10 is contemplated by the present disclosure as user interface 24.

Figure 5:
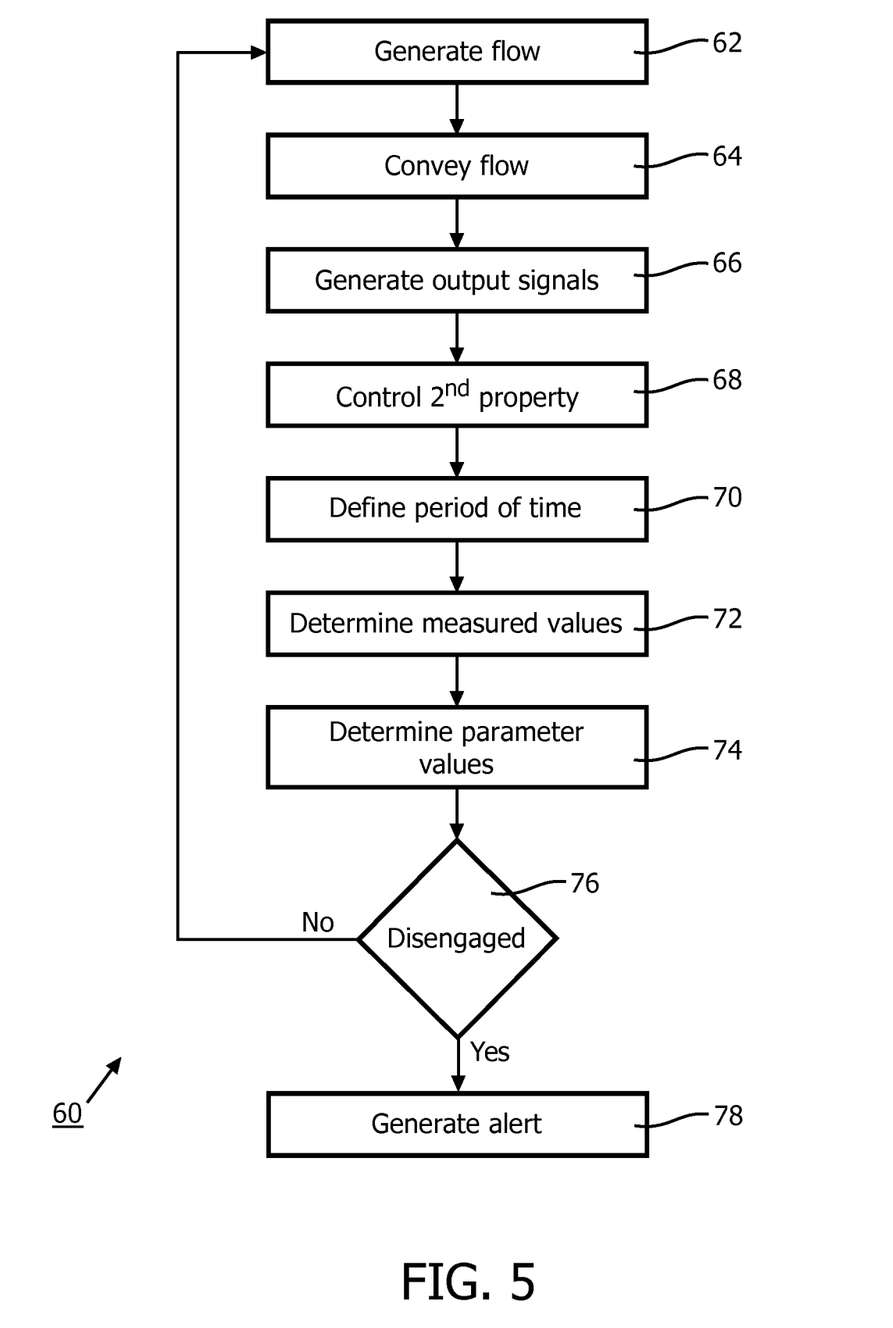
FIG. 5 illustrates a method of providing a flow of breathable gas.

FIG. 5 illustrates a method 60 of providing external notifications of events that take place within a virtual space. The operations of method 60 presented below are intended to be illustrative. In some embodiments, method 60 may be accomplished with one or more additional operations not described, and/or without one or more of the operations discussed. Additionally, the order in which the operations of method 60 are illustrated in FIG. 5 and described below is not intended to be limiting.

In some embodiments, method 60 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 60 in response to instructions stored electronically on an electronic storage medium. The one or more processing devices may include one or more devices configured through hardware, firmware, and/or software to be specifically designed for execution of one or more of the operations of method 60.

At an operation 62, a flow of breathable gas is generated. In some implementations, operation 62 is performed by a pressure generator the same as or similar to pressure generator 14 (shown in FIG. 1 and described herein).

At an operation 64, the flow of breathable gas is conveyed to an airway of a subject. In some implementations, operation 64 is performed by a patient interface assembly the same as or similar to patient interface assembly 16 (shown in FIG. 1 and described herein).

At an operation 66, output signals are generate that convey information related to a first dynamic property of the flow of breathable gas. In some implementations, operation 66 is performed by one or more sensors the same as or similar to sensors 18 (shown in FIG. 1 and described herein).

At an operation 68, a second dynamic property of the flow of breathable gas is controlled in accordance with a therapy regime. In some implementations, operation 68 is performed by a control module the same as or similar to control module 32 (shown in FIG. 1 and described herein).

At an operation 70, a period of time during which the flow of breathable gas is generated is defined. In some implementations, operation 70 is performed by a period module the same as or similar to period module 34 (shown in FIG. 1 and described herein).

At an operation 72, measured values of the first dynamic property are determined based on the output signals. In some implementations, operation 72 is performed by a property determination module the same as or similar to property determination module 30 (shown in FIG. 1 and described herein).

At an operation 74, one or more parameter values are determined for one or more model parameters of a model that provides predicted values of the first dynamic property as a function the second dynamic property. The parameter values are determined by fitting predicted values of the first dynamic property to measured values of the first dynamic property for points of time that occurred in the period of time. In some implementations, operation 74 is performed by a model parameter module the same as or similar to model parameter module 36 (shown in FIG. 1 and described herein).

At an operation 76, a determination is made from the parameter value(s) and/or the fit between the predicted values and the measured values of the first dynamic property as to whether the patient interface assembly was engaged with the airway of the subject during the period of time. In some implementations, operation 76 is performed by a disconnect detection module the same as or similar to disconnect detection module 38 (shown in FIG. 1 and described herein). Responsive to a determination that the patient interface assembly was engaged with the airway of the subject, method 60 iterates for another period of time.

At an operation 78, responsive to a determination that the patient interface assembly was disengaged with the airway of the subject, an alert is generated. In some implementations, operation 78 is performed by an alert module the same as or similar to alert module 40 (shown in FIG. 1 and described herein).

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the description provided above provides detail for the purpose of illustration based on what is currently considered to be the most practical and preferred embodiments, it is to be understood that such detail is solely for that purpose and that the disclosure is not limited to the expressly disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

What is claimed is:

1. A ventilator comprising:
   a pressure generator configured to generate a flow of breathable gas for delivery to an airway of a subject;
   a patient interface assembly configured to convey the flow of breathable gas from the pressure generator to the airway of the subject;
   a sensor configured to generate output signals conveying information related to a first dynamic property of the flow of breathable gas;
   a processor configured to execute computer program modules, the computer program modules comprising:
      a control module configured to control the pressure generator to adjust a second dynamic property of the flow of breathable gas over time in accordance with a therapy regime;
      a property determination module configured to determine measured values of the first dynamic property of the flow of breathable gas during respiration of the subject such that measured values of the first dynamic property are determined for individual points of time in an ongoing manner;
      a model parameter module configured to determine, for individual periods of time, parameter values for a model parameter of a model that provides a predicted value of the first dynamic property at a point in time as a function of the second dynamic property at the same point in time, wherein the model parameter module is configured to determine a parameter value for the model parameter during a given period of time by fitting predicted values of the first dynamic property to measured values of the first dynamic property for points of time that occurred in the given period of time; and
      a disconnect detection module configured to determine whether the airway of the subject is engaged with the patient interface assembly to receive the flow of breathable gas based on the fitting of the predicted values of the first dynamic property to the measured values of the first dynamic property.

2. The system of claim 1, wherein the model parameter module is configured such that the model has two or more model parameters, and wherein the model parameter module is configured to determine, for the individual periods of time, parameter values for the two or more model parameters by the fitting of the values of the first dynamic property to the measured values of the first dynamic property.

3. The system of claim 1, wherein the model parameter module is configured such that the model is a model of the pressure generator and/or the patient interface assembly.

4. The system of claim 1, wherein the first dynamic property is flow rate and the second dynamic property is pressure.

5. The system of claim 1, wherein the fitting of the predicted values of the first dynamic property to the measured values of the first dynamic property is determined based on minimization of a sum of squares of a difference between predicted values of the first dynamic property and measured values of the first dynamic property for points of time that occurred in the given period of time.

6. The system of claim 5, wherein in response to a relatively high fitting value of the predicted values of the first dynamic property to the measured values of the first dynamic property, the disconnect detection module determines that the subject is disengaged with the patient interface assembly.

7. The system of claim 5, wherein in response to a relatively low fitting value of the predicted values of the first dynamic property and the measured values of the first dynamic property, the disconnect detection module determines that the subject is engaged with the patient interface assembly.

8. A method of determining whether a subject is receiving a flow of breathable gas from a ventilator, the method being implemented by a ventilator comprising a pressure generator, a patient interface assembly, one or more sensors, and one or more processors, the method comprising:
   generating, with the pressure generator, a flow of breathable gas for delivery to an airway of a subject;
   conveying the flow of breathable gas from the pressure generator to the airway of the subject through the patient interface assembly;
   generating, with the one or more sensors, output signals conveying information related to a first dynamic property of the flow of breathable gas;
   controlling, with the one or more processors, the pressure generator to adjust a second dynamic property of the flow of breathable gas over time in accordance with a therapy regime;
   determining, with the one or more processors, measured values of the first dynamic property of the flow of breathable gas during respiration of the subject such that measured values of the first dynamic property are determined for individual points of time in an ongoing manner;
   determining, with the one or more processors for individual periods of time, parameter values for a model parameter of a model that provides a predicted value of the first dynamic property at a point in time as a function of the second dynamic property at the same point in time, wherein determination of a parameter value for the model parameter during a given period of time includes fitting predicted values of the first dynamic property to measured values of the first dynamic property for points of time that occurred in the given period of time; and
   determining, with the one or more processors, whether the airway of the subject is engaged with the patient interface assembly to receive the flow of breathable gas based on the fitting of the predicted values of the first dynamic property to the measured values of the first dynamic property.

9. The method of claim 8, wherein the model has two or more model parameters, and wherein the method comprises determining, for the individual periods of time, parameter values for the two or more model parameters by the fitting of the predicted values of the first dynamic property to the measured values of the first dynamic property.

10. The method of claim 8, wherein the model is a model of the pressure generator and/or the patient interface assembly.

11. The method of claim 8, wherein the first dynamic property is flow rate and the second dynamic property is pressure.

12. The method of claim 8, wherein determining, with the one or more processors, the fitting of the predicted values of the first dynamic property to the measured values of the first dynamic property comprises minimization of a sum of squares of a difference between the predicted values of the first dynamic property and the measured values of the first dynamic property for points of time that occurred in the given period of time.

13. The method of claim 12, wherein in response to a relatively high fitting value of the predicted values of the first dynamic property to the measured values of the first dynamic property, the one or more processors determine that the subject is disengaged with the patient interface assembly.

14. The method of claim 12, wherein in response to a relatively low fitting value of the predicted values of the first dynamic property to the measured values of the first dynamic property, the one or more processors determine that the subject is engaged with the patient interface assembly.

15. A system for determining whether a subject is receiving a flow of breathable gas from a ventilator, the system comprising:
    means for generating a flow of breathable gas for delivery to an airway of a subject;
means for conveying the flow of breathable gas from the pressure generator to the airway of the subject;
    means for generating output signals conveying information related to a first dynamic property of the flow of breathable gas;
    means for controlling the pressure generator to adjust a second dynamic property of the flow of breathable gas over time in accordance with a therapy regime;
    means for determining measured values of the first dynamic property of the flow of breathable gas during respiration of the subject such that measured values of the first dynamic property are determined for individual points of time in an ongoing manner;
    means for determining, for individual periods of time, parameter values for a model parameter of a model that provides a predicted value of the first dynamic property at a point in time as a function of the second dynamic property at the same point in time, wherein the means for determining parameter values is configured to determine a parameter value for the model parameter during a given period of time by fitting predicted values of the first dynamic property to measured values of the first dynamic property for points of time that occurred in the given period of time; and
    means for determining whether the airway of the subject is engaged with the patient interface assembly to receive the flow of breathable gas based on the fitting of the predicted values of the first dynamic property to the measured values of the first dynamic property.

16. The system of claim 15, wherein the means for determining parameter values is configured such that the model has two or more model parameters, and wherein the means for determining parameter values is configured to determine, for the individual periods of time, parameter values for the two or more model parameters by the fitting of the predicted values of the first dynamic property to the measured values of the first dynamic property.

17. The system of claim 15, wherein the means for determining parameter values is configured such that the model is a model of the pressure generator and/or the patient interface assembly.

18. The system of claim 15, wherein the first dynamic property is flow rate and the second dynamic property is pressure.

19. The system of claim 15, wherein the means for determining the fitting of the predicted values of the first dynamic property to the measured values of the first dynamic property is configured such that the fitting comprises minimization of a sum of squares of a difference between predicted values of the first dynamic property to the measured values of the first dynamic property for points of time that occurred in the given period of time.

20. The system of claim 19, wherein in response to a relatively high fitting value of the predicted values of the first dynamic property to the measured values of the first dynamic property, the means for determining whether the airway of the subject is engaged with the patient interface assembly to receive the flow of breathable gas is configured to determine that the subject is disengaged with the patient interface assembly.

21. The system of claim 19, wherein in response to a relatively low fitting value of the predicted values of the first dynamic property to the measured values of the first dynamic property, the means for determining whether the airway of the subject is engaged with the patient interface assembly to receive the flow of breathable gas is configured to that the subject is engaged with the patient interface assembly.

* * * * *